United States Patent
Watanabe et al.

(10) Patent No.: US 8,953,744 B2
(45) Date of Patent: Feb. 10, 2015

(54) RADIATION IMAGE DETECTING DEVICE AND METHOD FOR DETECTING START OF IRRADIATION

(75) Inventors: Keita Watanabe, Ashigarakami-gun (JP); Kentaro Noma, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 385 days.

(21) Appl. No.: 13/362,857

(22) Filed: Jan. 31, 2012

(65) Prior Publication Data
US 2012/0201357 A1 Aug. 9, 2012

(30) Foreign Application Priority Data

Feb. 9, 2011 (JP) .................................. 2011-025851

(51) Int. Cl.
| | | |
|---|---|---|
| A61B 6/00 | (2006.01) | |
| H05G 1/64 | (2006.01) | |
| H04N 5/32 | (2006.01) | |
| H04N 5/232 | (2006.01) | |
| H04N 5/361 | (2011.01) | |

(52) U.S. Cl.
CPC ................ H04N 5/32 (2013.01); A61B 6/4233 (2013.01); H05G 1/64 (2013.01); H04N 5/232 (2013.01); H04N 5/361 (2013.01)
USPC ..................... 378/98.8; 250/370.09

(58) Field of Classification Search
CPC ........... H05G 1/60; H05G 1/64; A61B 6/4233
USPC ............. 378/19, 62, 91, 98.7, 98.8, 114–116; 250/370.09
See application file for complete search history.

(56) References Cited

U.S. PATENT DOCUMENTS

| | | | | |
|---|---|---|---|---|
| 5,693,948 | A * | 12/1997 | Sayed et al. ............. | 250/370.09 |
| 5,757,011 | A * | 5/1998 | Whitebook et al. ...... | 250/370.09 |
| 5,887,049 | A * | 3/1999 | Fossum ........................ | 378/98.8 |
| 6,208,710 | B1 * | 3/2001 | Nagai ........................... | 378/108 |
| 6,307,915 | B1 * | 10/2001 | Frojdh ......................... | 378/98.8 |
| 6,380,528 | B1 * | 4/2002 | Pyyhtia et al. ............. | 250/208.1 |
| 6,404,854 | B1 * | 6/2002 | Carroll et al. ............... | 378/98.8 |
| 6,459,765 | B1 * | 10/2002 | Ganin et al. ................. | 378/108 |

(Continued)

FOREIGN PATENT DOCUMENTS

| | | |
|---|---|---|
| JP | 2003126072 A | 5/2003 |
| WO | 2010150569 A1 | 12/2010 |

OTHER PUBLICATIONS

Notification of Reasons for Refusal, dated Feb. 6, 2013, issued in corresponding JP Application No. 2011-025851, 5 pages in English and Japanese.

*Primary Examiner* — Allen C. Ho
(74) *Attorney, Agent, or Firm* — Sughrue Mion, PLLC

(57) ABSTRACT

An FPD, being offline from an X-ray source, detects X-ray irradiation from the X-ray source to detect an X-ray image. The FPD includes pixels arranged in two dimensions, scan lines corresponding to respective rows of the pixels, signal lines corresponding to respective columns of the pixels, and switching elements provided to the respective pixels to allow performing accumulation operation or readout operation. At least one of the pixels is used as a detection pixel to detect a start of the X-ray irradiation. First and second voltage signals are obtained successively through the signal line to which the detection pixel is connected. The start of the X-ray irradiation is judged based on a difference between the first and second voltage signals.

16 Claims, 12 Drawing Sheets

(56) References Cited

U.S. PATENT DOCUMENTS

| | | | |
|---|---|---|---|
| 6,516,098 B2 * | 2/2003 | Nonaka | 382/274 |
| 6,594,339 B1 * | 7/2003 | Alving et al. | 378/98.7 |
| 6,797,960 B1 | 9/2004 | Spartiotis et al. | |
| 6,801,598 B2 * | 10/2004 | Tashiro et al. | 378/98.8 |
| 6,847,698 B2 * | 1/2005 | Kaifu et al. | 378/97 |
| 6,965,111 B2 * | 11/2005 | Endo | 250/370.11 |
| 6,972,411 B2 * | 12/2005 | Schick et al. | 250/370.11 |
| 7,016,466 B2 * | 3/2006 | Rinaldi et al. | 378/98.8 |
| 7,431,500 B2 * | 10/2008 | Deych et al. | 378/207 |
| 7,518,115 B2 * | 4/2009 | Yamaguchi | 250/370.09 |
| 7,561,667 B2 * | 7/2009 | Nakayama | 378/97 |
| 7,573,979 B2 * | 8/2009 | Taoka et al. | 378/98.8 |
| 7,592,577 B1 * | 9/2009 | Liu | 250/208.1 |
| 7,593,508 B2 * | 9/2009 | Tsuchiya | 378/114 |
| 7,659,517 B2 * | 2/2010 | Scheffer | 250/370.09 |
| 7,781,740 B2 * | 8/2010 | Ohta et al. | 250/370.09 |
| 7,822,179 B2 * | 10/2010 | Tsuji | 378/98.8 |
| 8,045,680 B2 * | 10/2011 | Taoka et al. | 378/114 |
| 8,119,990 B2 * | 2/2012 | Zeller | 250/370.09 |
| 8,130,909 B2 * | 3/2012 | Nishino et al. | 378/91 |
| 8,247,779 B2 * | 8/2012 | Kameshima et al. | 250/370.09 |
| 8,459,869 B2 * | 6/2013 | Enomoto | 378/207 |
| 8,476,597 B2 * | 7/2013 | Kuwabara | 250/370.08 |
| 8,542,796 B2 * | 9/2013 | Sato | 378/62 |
| 8,633,447 B2 * | 1/2014 | Watanabe | 250/370.09 |
| 8,637,832 B2 * | 1/2014 | Watanabe et al. | 250/394 |
| 2003/0086523 A1 | 5/2003 | Tashiro et al. | |
| 2010/0054405 A1 | 3/2010 | Taoka et al. | |

* cited by examiner

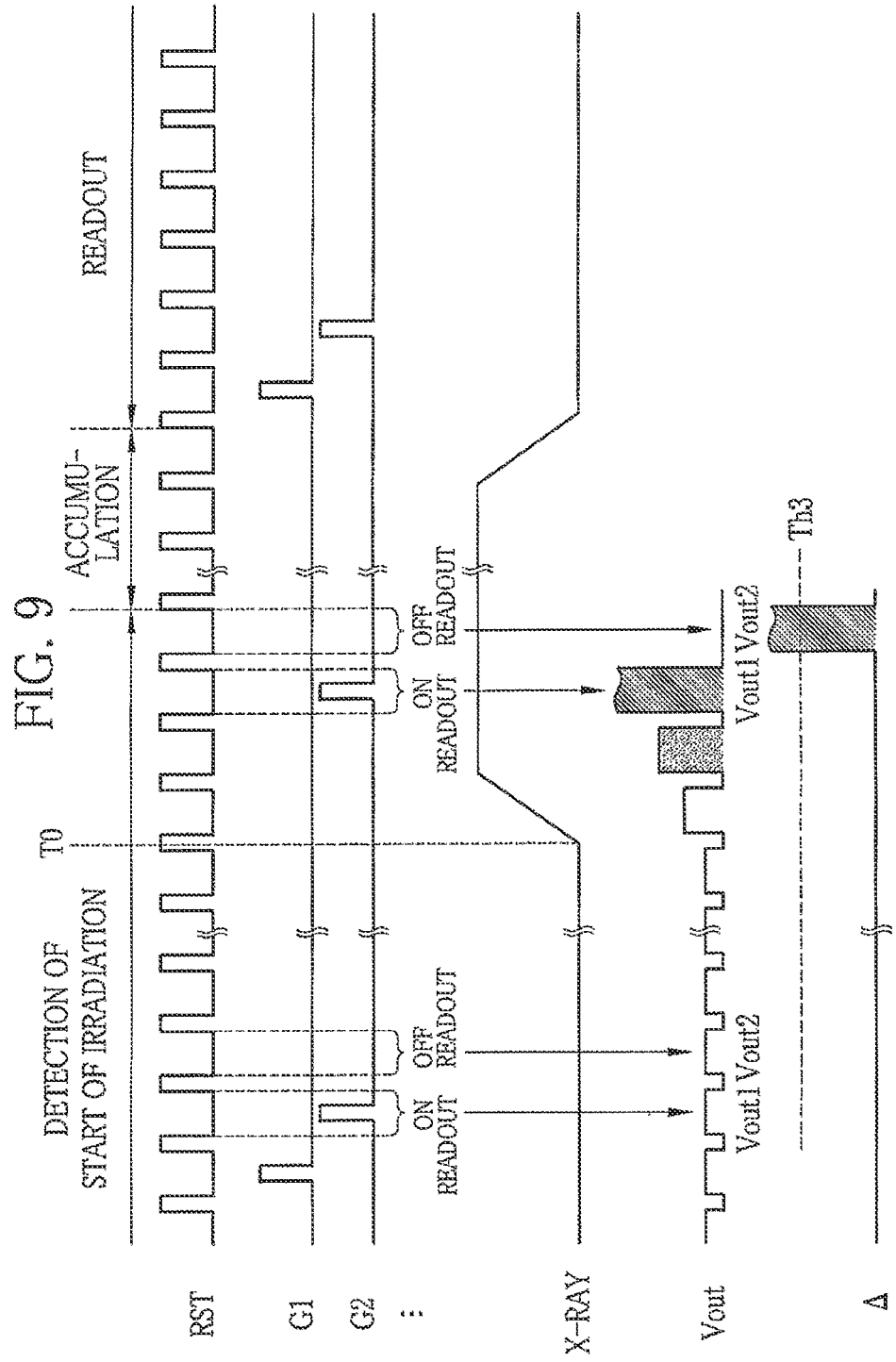

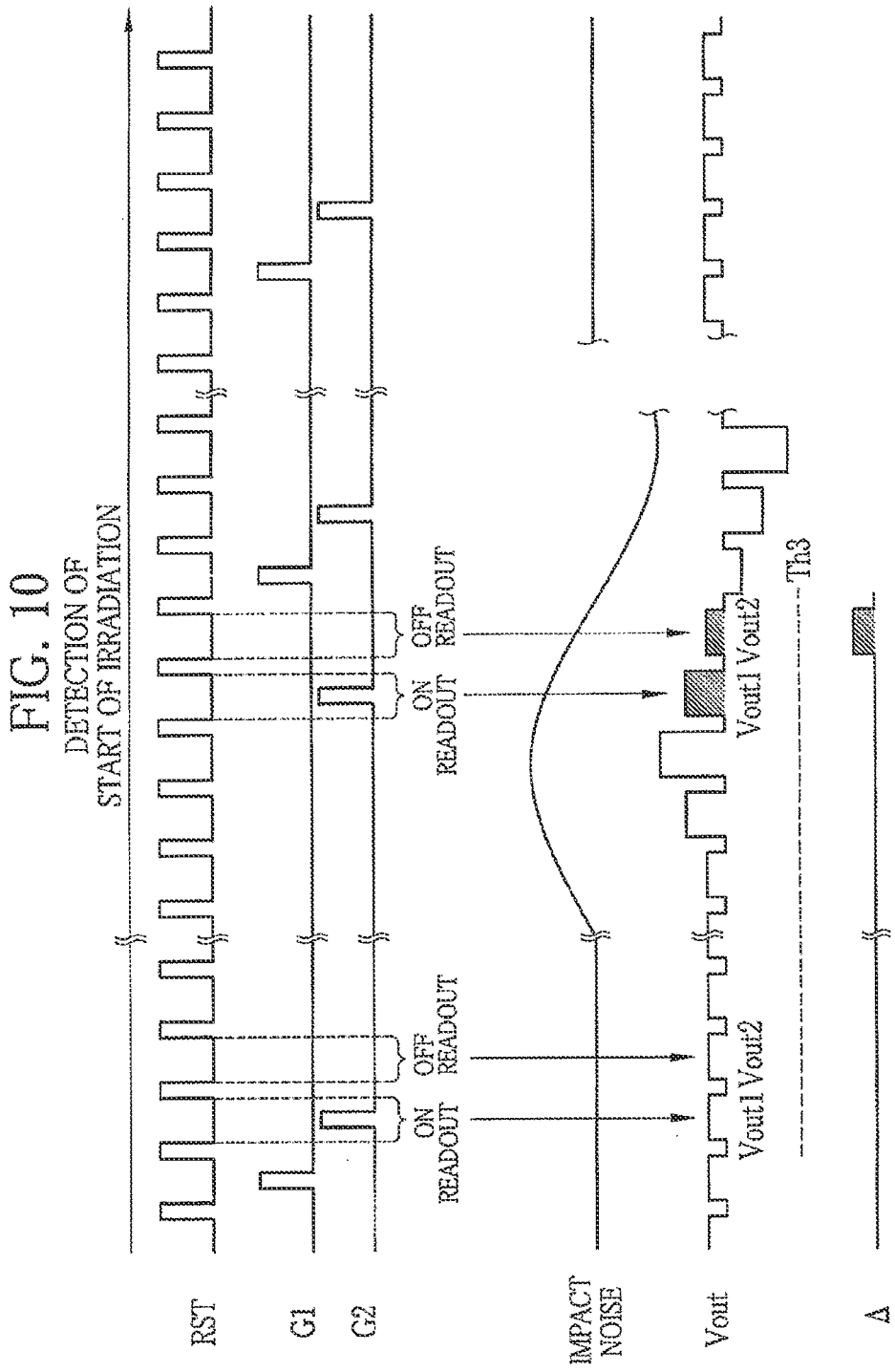

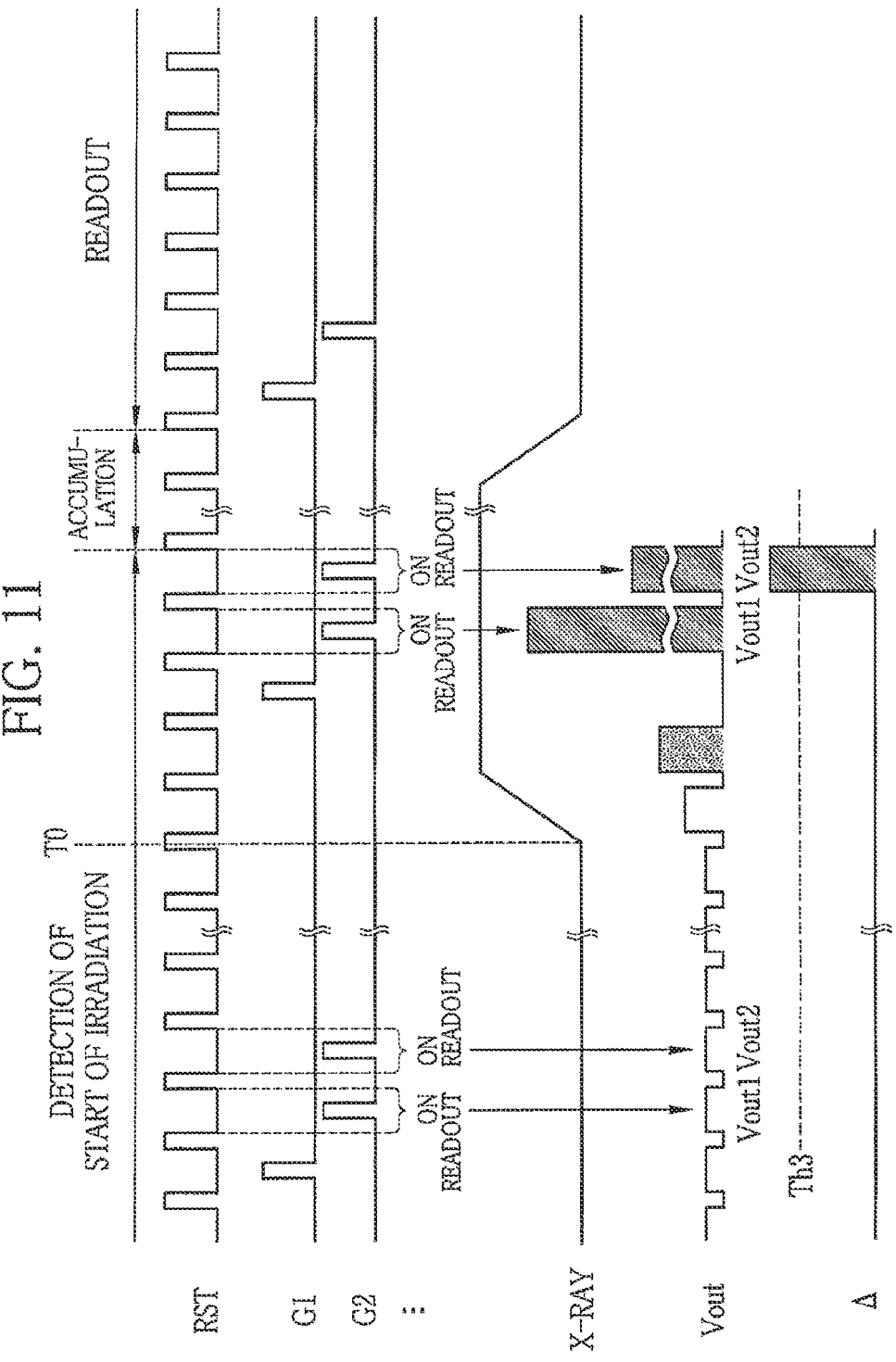

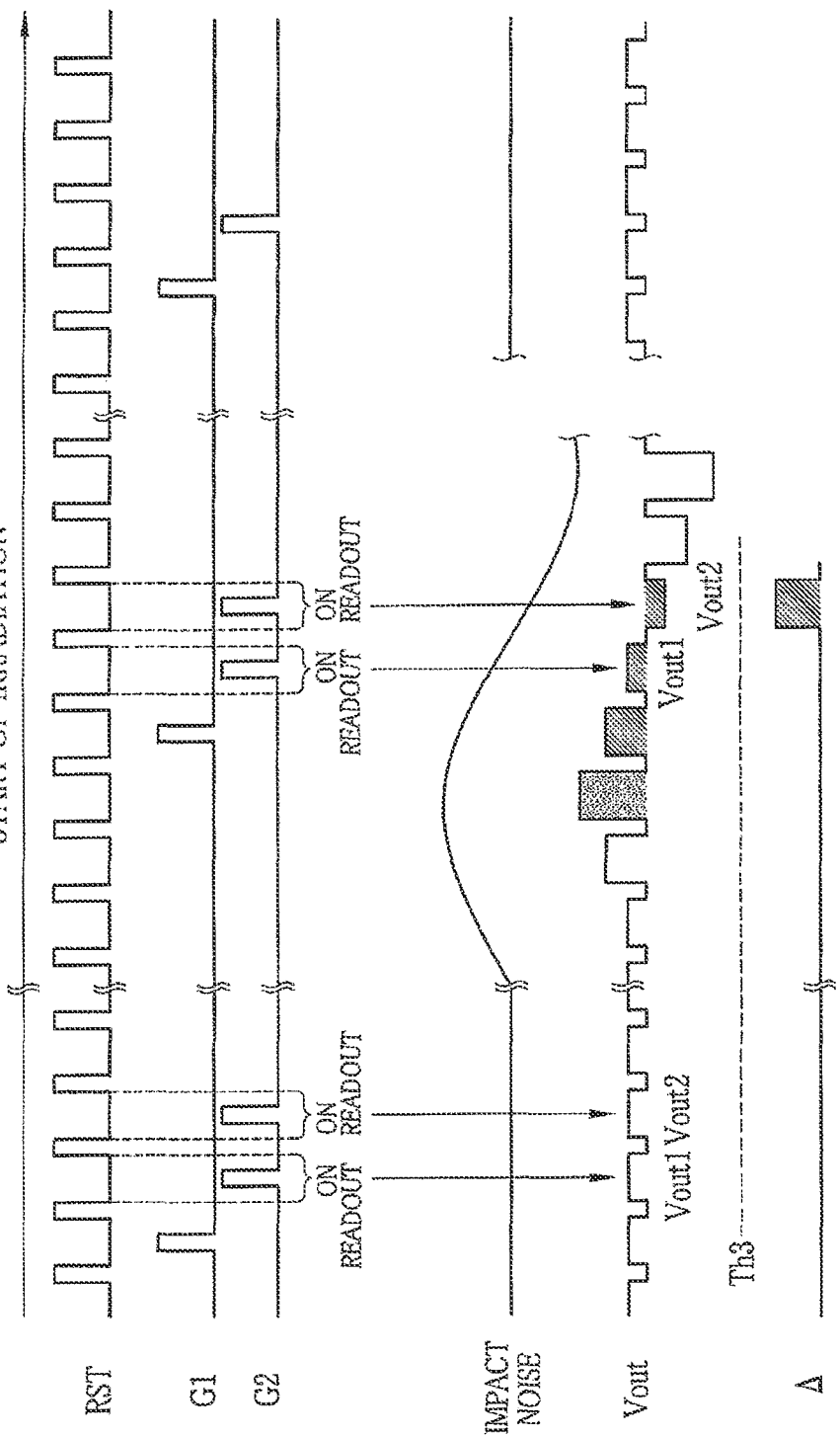

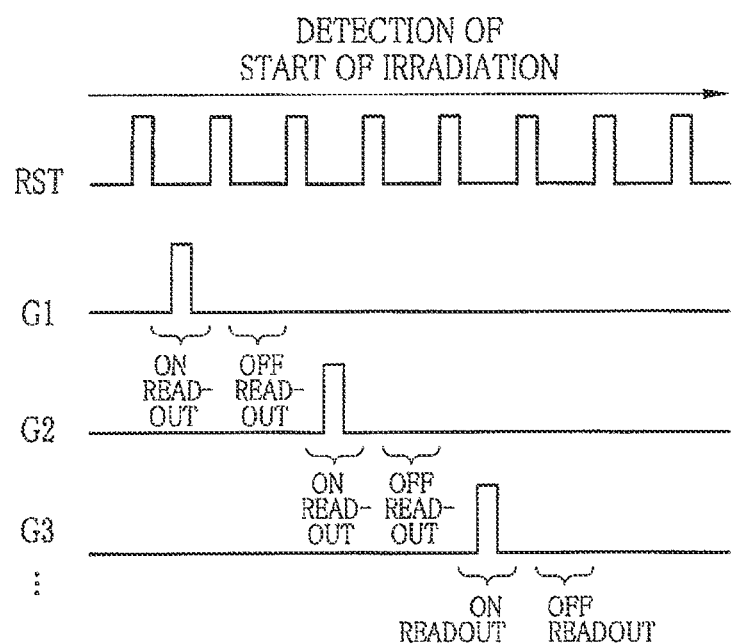
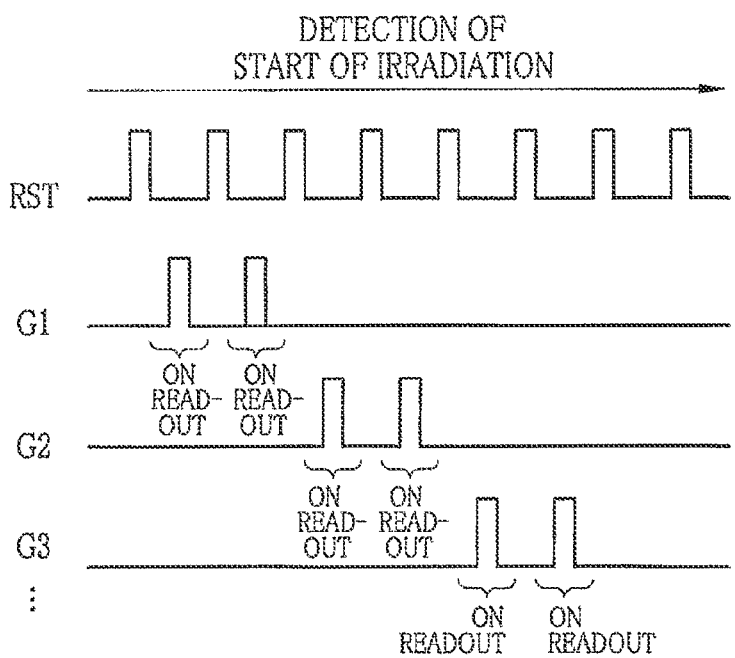

RADIATION IMAGE DETECTING DEVICE AND METHOD FOR DETECTING START OF IRRADIATION

BACKGROUND OF THE INVENTION

1. Field of the invention

The present invention relates to a radiation image detecting device for use in a radiation imaging system and a method for detecting start of irradiation with radiation.

2. Description Related to the Prior Art

In the medical field, a radiation imaging system using radiation, for example, X-rays, for image diagnosing has been known. The X-ray imaging system is composed of an X-ray source, an X-ray source controller, and an X-ray image detecting device. The X-ray source generates X-rays. The X-ray source controller controls the X-ray source. The X-ray image detecting device detects an X-ray image formed by the X-rays passed through a subject. An FPD (flat panel detector) is used as an X-ray image detecting device. The FPD includes a TFT (thin film transistor) active matrix substrate with a plurality of pixels arranged thereon. Each pixel accumulates signal charge corresponding to an amount of X-rays incident on the pixel. Thereby, the FPD detects an X-ray image representing image information of the subject, and outputs the X-ray image as digital image data.

The X-ray image detecting device using the FPD, unlike that using a film or an IP (imaging plate), needs to be synchronized with the X-ray source such that the FPD accumulates signal charge (hereinafter referred to as the accumulation operation) concurrently with the X-ray emission from the X-ray source. Accordingly, a controller, for example, a console of the X-ray image detecting device synchronizes the start of the accumulation operation by the FPD with the start of the X-ray emission by the X-ray source. The X-ray emission by the X-ray source is triggered by an emission start switch connected to the X-ray source controller. Namely, the controller receives an emission start signal from the emission start switch, and outputs this signal as a synchronization signal to the X-ray image detecting device. Upon receiving the synchronization signal, the X-ray image detecting device starts the accumulation operation to capture an X-ray image.

However, when the X-ray image detecting device and the X-ray source controller are manufactured by different makers, a synchronization control interface of the X-ray image detecting device or its controller may be incompatible with that of the X-ray source in the specifications of a cable and a connector, the format of the synchronization signal, and the like. To avoid this, various self-detection techniques for the X-ray image detecting device are proposed to detect the start of X-ray irradiation without using the synchronization signal so as to synchronize with the X-ray source (see U.S. Patent Application Publication No. 2003/0086523 corresponding to Japanese Patent Laid-Open Publication No. 2003-126072, U.S. Pat. No. 6,797,960 corresponding to Japanese translation No. 2002-543684 of PCT International Publication, U.S. Patent Application Publication No. 2010/0054405 A1, now U.S. Pat. No. 8,045,680 B2, corresponding to Japanese Patent Laid-Open Publication No. 2008-125903).

According to the self-detection techniques disclosed in the above patent documents, the X-ray image detecting device may erroneously detect the start of the X-ray irradiation when noise (hereinafter referred to as the impact noise) caused by impact, vibration, or the like occurs, which triggers a detection process of an X-ray image. However, the above patent documents do not describe or even suggest the problem of the false detection due to the impact noise and measures against it.

SUMMARY OF THE INVENTION

An object of the present invention is to provide a radiation image detecting device and a method for preventing false detection of start of irradiation with radiation due to impact noise.

The radiation image detecting device of the present invention includes a plurality of pixels, a plurality of scan lines, a plurality of signal lines, a drive section, and a controller. The pixels are arranged in two-dimensions along a row and column directions in an imaging area. Each of the pixels generates signal charge corresponding to an amount of the radiation incident on the pixel. Each of the pixels has a switching element for controlling reading of the signal charge. The scan lines extend in the row direction. Each of the scan lines is connected to respective gate electrodes of the switching elements of the corresponding pixels. The signal lines extend in the column direction. Each of the signal lines is connected to the corresponding pixels through the switching elements. The drive section turns off the switching element of the pixel to allow performing accumulation operation in which the signal charge generated in the pixel is accumulated. The drive section turns on the switching element of the pixel to allow performing readout operation. In the readout operation, the signal charge accumulated is read out through the signal line connected to the pixel. The controller uses at least one of the pixels as a detection pixel for detecting start of irradiation with the radiation. The controller successively obtains two output values, being first and second signal values, from the signal line to which the detection pixel is connected. The controller judges the start of the irradiation based on a difference between the first and second signal values. The controller controls the drive section based on the judgment.

It is preferable that the controller obtains a first difference between the first and second signal values, and judges that the irradiation is started when the first difference is greater than or equal to a first threshold value.

It is preferable that the controller carries out a starting step, a continuing step, an aborting step. In the starting step, the accumulation operation is started through the drive section when the output value of the signal line reaches greater than or equal to a second threshold value during irradiation detecting operation. In the continuing step, the accumulation operation is continued for a predetermined time to obtain a radiological image when it is judged, after a start of the accumulation operation, that the irradiation is started. In the aborting step, the accumulation operation is aborted and the irradiation detecting operation is resumed when the controller judges that the irradiation is not started.

It is preferable that the controller carries out a starting step. In the starting step, the accumulation operation is started through the drive section to obtain the radiological image when the controller judges the irradiation is started during the irradiation detecting operation.

It is preferable that the first signal value is obtained when the switching element of the detection pixel is in an ON state, and the second signal value is obtained when the switching element of the detection pixel is in an OFF state.

It is preferable that the first and second signal values are obtained when the switching element is in an ON state.

It is preferable that the two or more of the pixels are used as the detection pixels. It is preferable that the detection pixel is located close to a center of the imaging area.

It is preferable that the signal line is connected to an integrating amplifier for converting signal charge into a voltage signal.

It is preferable that the radiation image detecting device further includes a correction section for correcting a pixel value of the pixels of a row in which the detection pixel is located.

A method for detecting start of irradiation with radiation from a radiation source to a radiation image detecting device includes a using step, an obtaining step, a judging step, and a controlling step. In the using step, at least one of the pixels is used as a detection pixel. In the obtaining step, output values, being a first and second signal values, of a signal line to which the detection pixel is connected are obtained successively. In the judging step, the start of the irradiation is judged based on a difference between the first and second signal values. In the controlling step, the accumulation operation of each of the pixels is controlled in accordance with a result of the judgment.

It is preferable that it is judged that the irradiation is started when the difference is greater than or equal to a first threshold value.

It is preferable that the first signal value is obtained when the switching element is in an ON state, and the second signal value is obtained when the switching element is in an OFF state.

It is preferable that the first and second signal values are obtained when the switching element is in an ON state.

It is preferable that the method further includes a starting step, a continuing step, and an aborting step. In the starting step, the accumulation operation is started through the drive section when the output value of the signal line reaches greater than or equal to a second threshold value during irradiation detecting operation. In the continuing step, the accumulation operation is continued for a predetermined time to obtain the radiological image when it is judged, after a start of the accumulation operation, that the irradiation is started. In the aborting step, the accumulation operation is aborted and the irradiation detecting operation is started when it is judged that the irradiation is not started.

It is preferable that the method further includes a starting step. In the starting step, the accumulation operation is started through the drive section to obtain the radiological image when it is judged that the irradiation is started during the irradiation detecting operation.

According to the present invention, the start of the irradiation with radiation is detected accurately while false detection due to impact noise is prevented.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 9 is a timing chart showing a signal waveform formed by X-ray irradiation in a third embodiment;

FIG. 10 is a timing chart showing a signal waveform formed by impact noise in the third embodiment;

FIG. 11 is a timing chart showing a signal waveform formed by the X-ray irradiation in a fourth embodiment;

FIG. 12 is a timing chart showing a signal waveform formed by impact noise in the fourth embodiment;

FIG. 13 is a timing chart showing calculation of a difference $\Delta$ between a voltage signal Vout1 obtained by ON readout of pixels of every row and a voltage signal Vout2 obtained by OFF readout; and FIG. 14 is a timing chart showing calculation of a difference $\Delta$ between the voltage signal Vout1 obtained by ON readout of pixels of every row and the voltage signal Vout2 obtained by ON readout.

DESCRIPTION OF THE PREFERRED EMBODIMENTS (First Embodiment)

Figure 1:
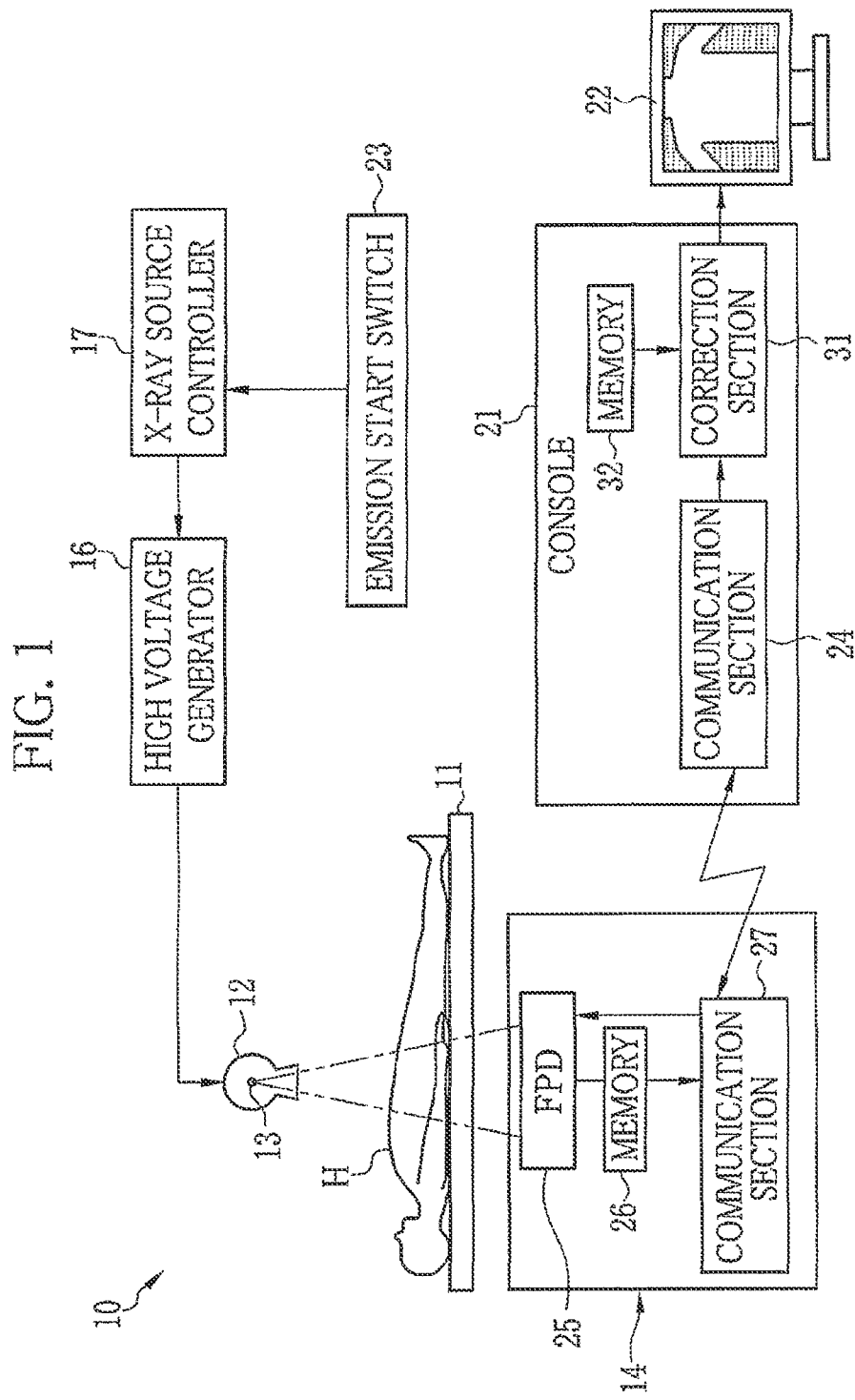
FIG. 1 is a schematic view showing an X-ray imaging system.

In FIG. 1, a radiation imaging system for obtaining a radiological image, for example, an X-ray imaging system 10 is provided with an imaging table 11, an X-ray source 12, and an electronic cassette (radiation image detecting device) 14. The imaging table 11 supports a subject (patient) H. The X-ray source 12 applies X-rays from an X-ray focal point 13 to the subject H. The electronic cassette 14 detects an X-ray image formed by the X-rays passed through the subject H. The X-ray source 12 has an X-ray tube and a collimator. The X-ray tube generates the X-rays. The collimator limits an irradiation field of the X-rays.

The X-ray imaging system 10 includes a high voltage generator 16, an X-ray source controller 17, a console 21, and a monitor 22. Imaging conditions such as a tube voltage, a tube current, and an emission time are inputted to the X-ray source controller 17 through an operation panel (not shown), for example. The X-ray source controller 17 sends the imaging conditions to the high voltage generator 16. An emission start switch 23 is connected to the X-ray source controller 17. The emission start switch 23 inputs an emission start signal to the X-ray source controller 17. The X-ray source controller 17 sends the emission start signal to the X-ray source 12 through the high voltage generator 16.

The high voltage generator 16 generates the tube voltage and the tube current according to the imaging conditions inputted from the X-ray source controller 17. The tube voltage and the tube current are supplied to the X-ray source 12. In response to the emission start signal, the X-ray source 12 starts emitting X-rays in accordance with the tube voltage and the tube current supplied. The X-ray source 12 stops emitting the X-rays when the emission time elapses.

The console 21 controls the electronic cassette 14. The emission start signal from the emission start switch 23 is not inputted to the console 21. The console 21 sends a control signal to the electronic cassette 14 through a communication section 24, and receives X-ray image data detected by the electronic cassette 14. The monitor 22 displays the X-ray image received by the console 21. The monitor 22 displays an operation screen for operating the console 21.

The console 21 has a correction section 31. The correction section 31 performs various image processes to the X-ray image data inputted from the electronic cassette 14. Then the X-ray image data is outputted to the monitor 22. The correction section 31 performs a defect correction process and a noise removal process, for example. In the defect correction process, a pixel value of a defective pixel is corrected by interpolation. In the noise removal process, a noise component caused by dark charge is removed by subtracting offset image data from the X-ray image data. The offset image data and the defective pixel data are stored in advance in the memory 32. Note that a gain correction process for adjusting an output value of each pixel is performed by a signal processing circuit of the electronic cassette 14. The gain correction process is performed based on the imaging conditions, for example.

The electronic cassette 14 includes an FPD 25 (flat panel detector), a memory 26, and a communication section 27. The FPD 25 detects an X-ray image. The memory 26 temporarily stores X-ray image data outputted from the FPD 25. The communication section 27 communicates with the console 21 to send the data in the memory 26 and receive the control signal. The FPD 25, the memory 26, and the communication section 27 are contained in a flat rectangular parallel-piped housing, for example. The communication section 27 communicates wirelessly using light such as infrared light or radio waves. The electronic cassette 14 is of a wireless type that contains a battery (not shown) for supplying power to each section including the FPD 25. Note that the communication sections 24 and 27 may communicate through a cable. Instead of the battery, a commercial power source may supply power to the electronic cassette 14 through a power cable.

Figure 2:
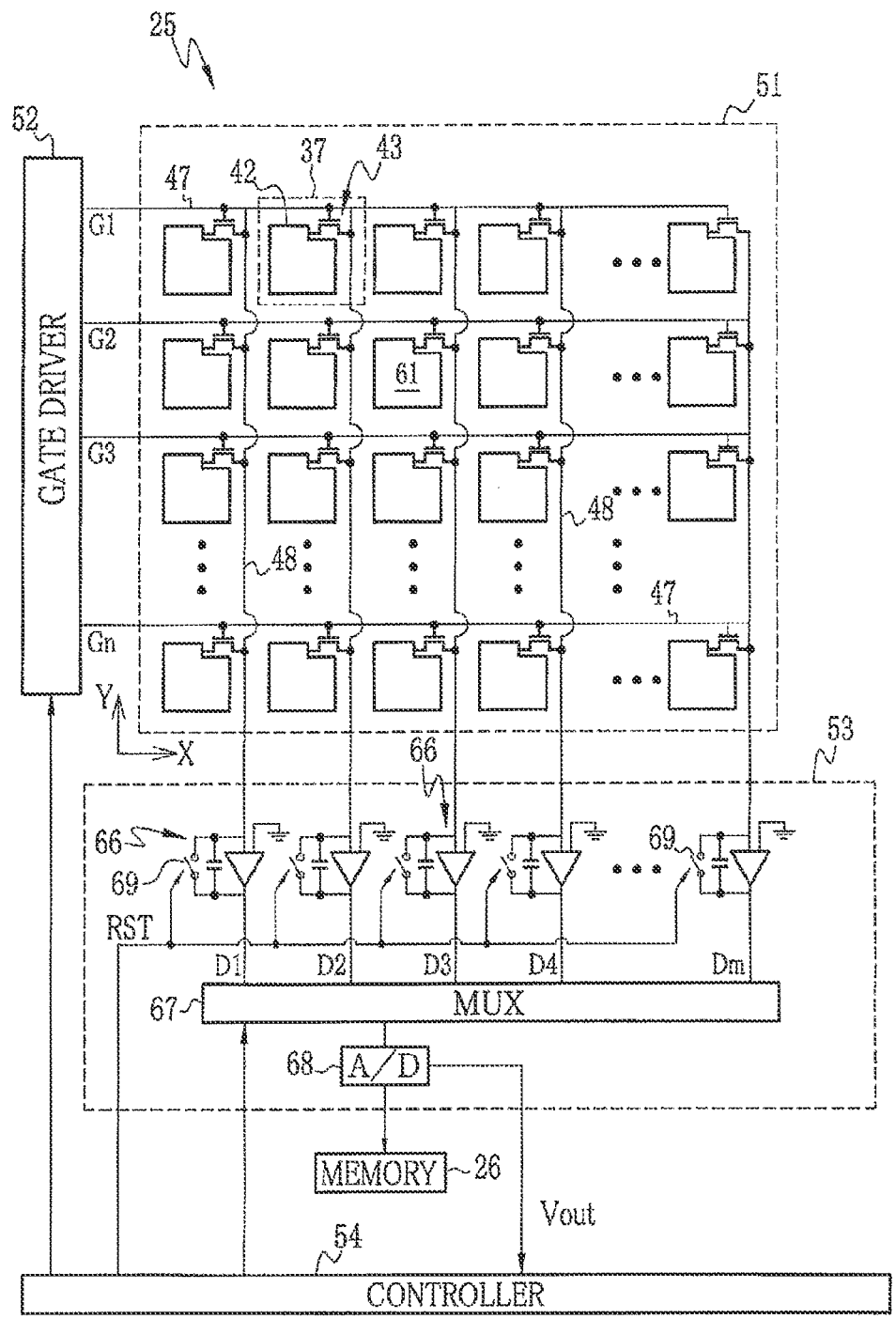
FIG. 2 is an explanatory view showing an electronic cassette.

In FIG. 2, the FPD 25 has an imaging area (imaging panel) 51, a gate driver 52, a signal processing circuit 53, and a controller 54. The imaging area 51 has a plurality of pixels 37 arranged on a TFT active matrix substrate. Each pixel 37 accumulates signal charge corresponding to the amount of the X-rays incident on the pixel. The gate driver 52 drives the pixels 37, and controls reading of the signal charge. The signal processing circuit 53 converts the signal charge read out from the pixels 37 into pixel data, and outputs the pixel data. The controller 54 controls the gate driver 52 and the signal processing circuit 53 to control the operation of the FPD 25. The pixels 37 are arranged at a predetermined pitch in a two-dimensional matrix with n rows (X direction) and m columns (Y direction).

The FPD 25 is of an indirect conversion type with a scintillator (phosphor) for converting the X-rays into visible light. The pixels 37 convert the visible light photoelectrically. The scintillator is disposed to face the entire imaging area 51 in which the pixels 37 are arranged.

Each pixel 37 includes a photodiode 42, a capacitor (not shown), and a thin film transistor (TFT) 43 being a switching element. The photodiode 42 is a photoelectric conversion element that generates electric charge upon incidence of visible light on the photodiode 42. The capacitor accumulates the electric charge generated.

The photodiode 42, for example, a PIN photodiode has a semiconductor layer for generating the electric charge (negative-electron and positive-hole pairs) and upper and lower electrodes disposed on the top and bottom of the semiconductor layer. The TFT 43 is connected to the lower electrode of the photodiode 42. A bias line (not shown) is connected to the upper electrode. A bias voltage is applied to the upper electrode through the bias line, which produces an electric field in the semiconductor layer. The electric charge, that is, the negative-electrons and the positive-holes generated in the semiconductor layer by the photoelectric conversion are attracted to the upper and lower electrodes with positive and negative polarity, respectively. Thereby, the electric charge is accumulated in the capacitor.

A gate electrode of the TFT 43 is connected to a scan line 47. A source electrode of the TFT 43 is connected to the photodiode 42, and a drain electrode is connected to a signal line 48. The scan lines 47 and the signal lines 48 are arranged in a lattice shape. The number of the scan lines 47 coincides with the number "n" of the rows of the pixels 37 arranged in the imaging area 51. The number of the signal lines 48 coincides with the number "m" of the columns of the pixels 37. The scan lines 47 are connected to the gate driver 52. The signal lines 48 are connected to the signal processing circuit 53.

The gate driver 52 drives the TFTs 43 to carry out an accumulation operation, a readout operation, or a pixel reset operation. In the accumulation operation, each pixel 37 accumulates the signal charge corresponding to the amount of the X-rays incident on the pixel 37. In the readout operation, the signal charge is read out from the pixels 37. In the semiconductor layer of the photodiode 42, the dark charge occurs irrespective of the presence or absence of the incident X-rays. Since the bias voltage is applied to the semiconductor layer, the dark charge accumulates in the capacitor. In the pixel reset operation, the dark charge in each pixel 37 is discharged through the signal line 48 to reset the pixel 37. Based on the control signal inputted from the console 21 through the communication section 27, the controller 54 controls the operation timing of the pixel reset operation, the accumulation operation, and the readout operation, which are carried out by the gate driver 52.

In the accumulation operation, the pixel 37 accumulates the signal charge while the TFT 43 is turned off. Concurrently with the start of the accumulation operation, the controller 54 actuates a timer to count up a charge accumulation time. The charge accumulation time is set longer than the maximum emission time of the X-ray source 12 so that the charge accumulation continues throughout the X-ray emission. In the readout operation, the gate driver 52 sequentially generates gate pulses G1 to Gn, being drive pulses for driving the TFTs 43, to activate the respective scan lines 47. Thereby, the TFTs 43, connected to the activated scan line 47, are turned on from row to row. When the TFT 43 is turned on, the electric charge accumulated in the capacitor of the pixel 37 is read out to the signal line 48, and then inputted to the signal processing circuit 53.

The signal processing circuit 53 includes integrating amplifiers 66, a multiplexer (MUX) 67, and an A/D converter 68. The integrating amplifiers 66 are connected to the signal lines 48, respectively. The integrating amplifier 66 is composed of an operational amplifier and a capacitor. The capacitor is connected between input and output terminals of the operational amplifier. One of the input terminals of the operational amplifier is connected to the signal line 48. The other input terminal is connected to a ground (GND). The integrating amplifiers 66 integrate the electric charge inputted from the signal lines 48 and then convert the electric charge into voltage signals D1 to Dm, and output the voltage signals D1 to Dm, respectively. The output terminal of every integrating amplifier 66 is connected to the MUX 67. An output of the MUX 67 is connected to the A/D converter 68.

The MUX 67 sequentially selects each of the integrating amplifiers 66 connected in parallel, and inputs the voltage signals D1 to Dm in series in the selected order to the A/D converter 68. The A/D converter 68 converts each of the voltage signals D1 to Dm into digital data, and outputs the digital data to the memory 26 contained in the housing of the electronic cassette 14.

After the MUX 67 reads out the voltage signals D1 to Dm of the single row from the respective integrating amplifiers 66, the controller 54 outputs a reset pulse (reset signal) RST to each of the integrating amplifiers 66. In response to the reset pulse RST, a reset switch 69 of each of the integrating amplifiers 66 is turned on to reset the voltage signals D1 to Dm accumulated in the integrating amplifiers 66 of the single row (for example, the voltage signals D1 to Dm correspond to the pixels 37 of a first row connected to the scan line G1). Subsequently, the controller 54 commands the gate driver 52 to output the gate pulse G2 to a second row, and thereby the signal charge is read out from the pixels 37 of the second row. The readout operation of the second or later rows is carried out in a like manner as that of the first row.

When the readout operation of every row is completed, image data representing a single frame of the X-ray image is recorded to the memory 26. Then, the image data is read out from the memory 26, and outputted to the console 21 through the communication section 27. Thereby, the X-ray image of the subject H is detected.

Because the dark charge in the pixels 37 causes offset noise in the pixel data, the pixel reset operation is performed before the accumulation operation. A sequential reset method in which the pixels 37 are reset on a row-by-row basis, for example, may be used in the pixel reset operation.

In the sequential reset method, the gate driver 52 issues the gate pulses G1 to Gn to the scan lines 47, sequentially and respectively. Thereby, the TFTs 43 of the pixels 37 are turned on from row to row. While the TFTs 43 are turned on, the dark charge flows from the pixels 37 to the integrating amplifiers 66 through the signal lines 48. In the pixel reset operation, unlike the readout operation, the MUX 67 does not read the signal charge accumulated in the integrating amplifiers 66. Instead, the controller 54 outputs the reset pulses RST in synchronization with the generation of gate pulses G1 to Gn, to reset the integrating amplifiers 66, respectively.

The FPD 25 is provided with a plurality of pixels 37. At least one of the pixels 37 is used as a detection pixel 61 for detecting the start of X-ray irradiation. During the irradiation detecting operation, the signal charge generated in the detection pixel 61 accumulates in the capacitor when the TFT 43 is turned off. When the TFT 43 is turned on, the signal charge in the detection pixel 61 is read out to the signal line 48. The TFT 43 of the detection pixel 61 is turned on or off, together with the TFTs 43 of the pixels 37 of the same row, by one of the gate pulses G1 to Gn (G2 in FIG. 2) inputted to the scan line 47 to which the detection pixel 61 is connected. Irrespective of the operational state of the electronic cassette 14, the voltage signal (D3 in FIG. 2), outputted from the integrating amplifier 66 on the signal line 48 to which the detection pixel 61 is connected, is inputted as a voltage signal Vout to the controller 54 through the A/D converter 68.

During the X-ray irradiation, the voltage signal Vout of the integrating amplifier 66 connected to the signal line 48 of the detection pixel 61 increases. The voltage signal Vout also increases when the impact noise occurs. The X-ray irradiation cannot be distinguished from the impact noise merely by the increase in the voltage signal Vout. However, as it is apparent from a comparison between the FIGS. 3 and 4, the voltage signal Vout generated by the X-ray irradiation and that by the impact noise behave differently after they increase. The X-ray irradiation is surely distinguished from the impact noise based on the history of change in each of the voltage signals Vout. When it is determined that the change in the voltage signal Vout is caused by the X-ray irradiation, the charge accumulation in each pixel 37 is started to detect (capture) an X-ray image. Thus, the false detection due to the impact noise is prevented.

Because the history of the change in the voltage signal Vout is used for distinguishing the X-ray irradiation from the impact noise, this determination takes time. When the accumulation operation of the pixels 37 is started after the determination that the X-ray irradiation takes place, only a part of the X-rays emitted from the X-ray source 12 is used for the X-ray image detection and the remaining is wasted. This reduces the charge accumulated in each pixel 37, deteriorating the SN ratio of the pixel signal.

In the present invention, to prevent the waste of the X-rays and to improve the image quality, it is regarded that the X-ray irradiation takes place when the voltage signal Vout changes during the irradiation detecting operation and this triggers the accumulation operation in each pixel 37. During the accumulation operation, the history of the change in the voltage signal Vout is checked to judge whether the change in the voltage signal Vout is caused by the X-ray irradiation or the impact noise. When it is judged that the change is caused by the X-ray irradiation, the accumulation operation is continued. When it is judged that the change is caused by the impact noise, the accumulation operation is aborted.

Based on the voltage signal Vout from the detection pixel 61, the controller 54 switches from the irradiation detecting operation to the accumulation operation, distinguishes the X-ray irradiation from the impact noise, and decides whether to continue the accumulation operation, which will be described in the following.

When the irradiation detecting operation is started, first, the controller 54 monitors the value of the voltage signal Vout. The controller 54 compares the voltage signal Vout with a predetermined threshold value Th1. The controller 54 regards or provisionally determines that the X-ray irradiation is started when the voltage signal Vout reaches greater than or equal to the threshold value Th1.

Upon this provisional determination, the controller 54 turns off the TFTs 43 of all the pixels 37 including the detection pixel 61. Thereby, the irradiation detecting operation is switched to the accumulation operation.

During the accumulation operation, when the TFTs 43 are turned on, the controller 54 obtains the voltage signal Vout corresponding to the signal charge read out from the detection pixel 61. Subsequently, after the TFTs 43 are turned off, the controller 54 obtains the voltage signal Vout from the integrating amplifier 66 on the signal line 48 to which the detection pixel 61 is connected. Namely, the controller 54 sequentially obtains a first voltage signal Vout (hereinafter referred to as the voltage signal Vout1) when the TFT 43 of the detection pixel 61 is in an ON state and a second voltage signal Vout (hereinafter referred to as the voltage signal Vout2) when the TFT 43 of the detection pixel 61 is in an OFF state.

Then, the controller 54 calculates or obtains the history of the change in the voltage signal Vout from the detection pixel 61, that is, a difference $\Delta(=Vout1-Vout2)$ between the voltage signals Vout1 and Vout2 and compares the difference $\Delta$ with a predetermined threshold value Th2. When the change in the voltage signal Vout is caused by the impact noise, the difference $\Delta$ takes a value of the order of noise caused by the dark charge, and remains less than the threshold value Th2. On the other hand, when the change in the voltage signal Vout is caused by the X-ray irradiation, the difference $\Delta$ takes a value greater than or equal to the threshold value Th2. Accordingly, when the difference $\Delta$ between the voltage signals Vout1 and Vout2 is less than the threshold value Th2, the controller 54 judges that the change in the voltage signal Vout is caused by the impact noise. When the difference Δ is greater than or equal to the threshold value Th2, the controller 54 judges that the change in the voltage signal Vout is caused by the X-ray irradiation.

The controller 54 controls the accumulation operation based on the above-described judgment result. To be more specific, when the judgment result is caused by the impact noise, the controller 54 immediately aborts the accumulation operation and resumes the irradiation detecting operation. On the other hand, when the judgment result is caused by the X-ray irradiation, the controller 54 allows performing the readout operation after the predetermined accumulation time specified by the imaging conditions elapses. Thus, an X-ray image is captured.

To capture an X-ray image using the X-ray source 12 and the electronic cassette 14, the imaging conditions are set to each of the X-ray source controller 17 and the electronic cassette 14. The imaging conditions include the tube voltage, the tube current, and the X-ray emission time. The tube voltage defines an energy spectrum of the X-rays applied from the X-ray source 12. The tube current defines an amount of X-ray irradiation per unit time. The imaging conditions vary depending on a portion to be imaged, age of the subject H, or the like.

The imaging conditions of the electronic cassette 14 is set through the console 21. The electronic cassette 14 sets a gain of the integrating amplifier 66 according to the imaging conditions. The console 21 is provided with various imaging menus with different imaging conditions. The imaging menus are displayed on the operation screen in a selectable manner. When an imaging menu is selected through the operation screen, the imaging conditions specified by the imaging menu are set to the electronic cassette 14.

When the electronic cassette 14 is powered on, the FPD 25 is in a standby state to wait for the command to start preparation for image capture. In the standby state, the gate driver 52 and the signal processing circuit 53 are operable in response to a command from the controller 54. In the standby state, for example, the pixel reset operation of the sequential reset method is carried out repeatedly. Note that, in the standby state, the irradiation detecting operation is not started. So, even if the voltage signal Vout takes a value greater than or equal to the threshold value Th1 due to impact noise or the like, the controller 54 does not allow switching to the accumulation operation.

When the imaging menu is selected through the console 21, the imaging conditions are inputted to the electronic cassette 14. The controller 54 takes the input of the imaging conditions as the command to start preparation for image capture, and starts the irradiation detecting operation. The controller 54 obtains the voltage signal Vout from the integrating amplifier 66 of a signal line 48 to which the detection pixel 61 is connected, and starts monitoring the voltage signal Vout.

Figure 3:
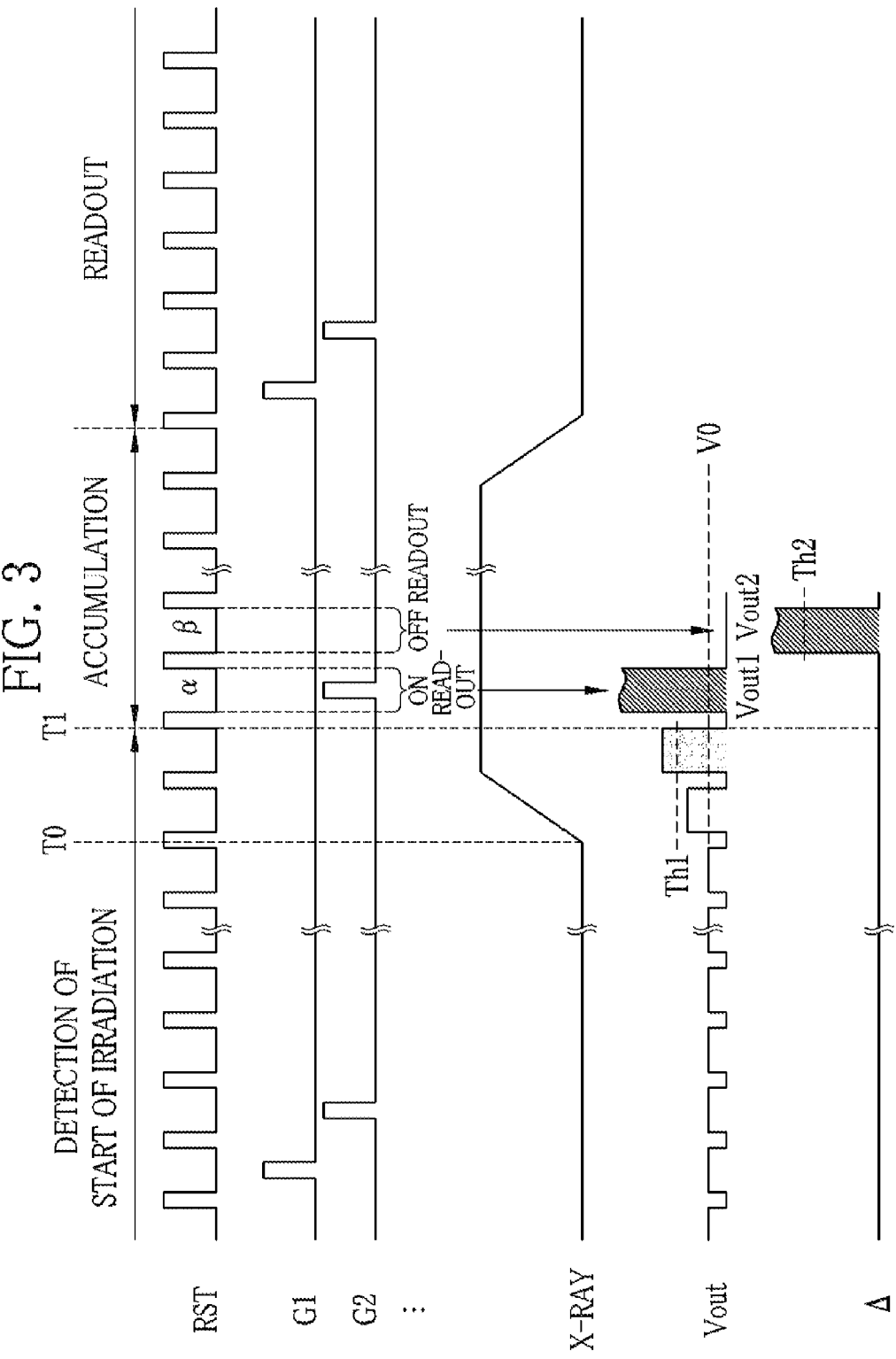
FIG. 3 is a timing chart showing a signal waveform formed by the X-ray irradiation.

As shown in FIG. 3, during the time between the start of the irradiation detecting operation and the start of the X-ray emission (time: T0), when the pixel reset operation is performed, the voltage signal Vout takes a value of noise (hereinafter referred to as the dark charge noise) caused by the dark charge. Accordingly, the threshold value Th1, used for starting the accumulation operation, is set to be greater than the dark charge noise.

After the emission start switch 23 is pressed at the time T0 to apply the X-rays from the X-ray source 12, the signal charge generated in the detection pixel 61 flows into the integrating amplifier 66 and thereby the value of the voltage signal Vout exceeds a noise level V0. The controller 54 compares the voltage signal Vout with the threshold value Th1. The controller 54 regards that the X-ray irradiation is started at the time T1 at which the voltage signal Vout is changed to a value greater than or equal to the threshold value Th1. Upon this provisional determination of the start of the X-ray irradiation, the controller 54 controls the gate driver 52 to turn off the TFT 43 of every pixel 37. Thereby, the accumulation operation is started from the time T1.

After the irradiation detecting operation is switched to the accumulation operation, the controller 54 commands the gate driver 52 to input the gate pulse (G2) to the scan line 47 to which the detection pixel 61 is connected, in synchronization with the first reset pulse RST inputted to the integrating amplifier 66. Thereby, the TFTs 43 of the pixels 37 (including the detection pixel 61) connected to the single row are turned on in a period α, that is, the first interval between the reset pulses RST after the transition to the accumulation operation. Thereby, the signal charge accumulated in the detection pixel 61 is read out to the integrating amplifier 66 in the period α. The voltage signal Vout, outputted from the integrating amplifier 66 in the period α, is inputted as the first voltage signal Vout1 to the controller 54. The first voltage signal Vout1 is used for judging whether the change in the voltage signal Vout is caused by the X-ray irradiation or the impact noise.

After the start of the accumulation operation, when the signal charge is read out from the detection pixel 61 with the TFT 43 in the ON state, the controller 54 stops inputting the gate pulse (G2) to the scan line 47 to which the detection pixel 61 is connected. Namely, in a period β, between the reset pulses RST after the period α, and the subsequent periods, the TFTs 43 of the pixels 37 (including the detection pixel 61) of the single row are turned off. Thereby, from the period β and on, accumulation of the signal charge in the pixels 37 (including the detection pixel 61) of the single row is started, only behind by the period α.

In the period α, the first voltage signal Vout1 is inputted to the controller 54. In the subsequent period β, the TFT 43 of the detection pixel 61 is kept in the OFF state, and the output value of the integrating amplifier 66 is inputted as the second voltage signal Vout2 to the controller 54. Accordingly, the signal charge generated in the detection pixel 61 is saved.

Throughout the successive readouts of the voltage signals Vout1 (with the TFT 43 turned on) and Vout2 (with the TFT 43 turned off), the TFTs 43 of the pixels 37 of the rows other than that of the detection pixel 61 are turned off. Thereby, on and after the time T1, the pixels 37 of the rows other than that of the detection pixel 61 keep accumulating the signal charge. Hereinafter, the readout of the voltage signal Vout from the detection pixel 61 when the TFT 43 is in the ON state is referred to as the ON readout. The readout of the voltage signal Vout from the detection pixel 61 when the TFT 43 is in the OFF state is referred to as the OFF readout.

The controller 54 calculates the difference Δ between the first voltage signal Vout1 (ON readout) and the second voltage signal Vout2 (OFF readout). In this embodiment, the first voltage signal Vout1 corresponds to the signal charge (including the dark charge) generated in the detection pixel 61 during the period α, and exceeds the threshold value Th1. On the other hand, in the second voltage signal Vout2 (OFF readout), the signal charge and the like generated in the detection pixel 61 during the period β is not inputted to the integrating amplifier 66, so the second voltage signal Vout2 is approximately "0". Accordingly, the difference Δ calculated by the controller 54 is approximately equivalent to the value of the first voltage signal Vout1.

The controller 54 compares the difference Δ with the threshold value Th2 to judge whether the change in the voltage signal Vout is caused by the X-ray irradiation or the impact noise. The threshold value Th2 is set such that the difference Δ is greater than or equal to the threshold value Th2 when the X-ray irradiation takes place, but less than the threshold value Th2 when the impact noise occurs.

Upon judging that the X-ray irradiation takes place, the controller 54 allows performing the accumulation operation for a predetermined duration time counted up from the time T1. Then the controller 54 allows performing the readout operation to output the X-ray image data. The duration time for performing the accumulation operation is specified by the emission time inputted. Note that the accumulation time for the pixels 37 of the row to which the detection pixel 61 belongs is shorter than that for the remaining pixels 37 by the period α.

On the other hand, when impact noise occurs in the electronic cassette 14 due to impact or vibration, the electronic cassette 14 operates as follows.

Figure 4:
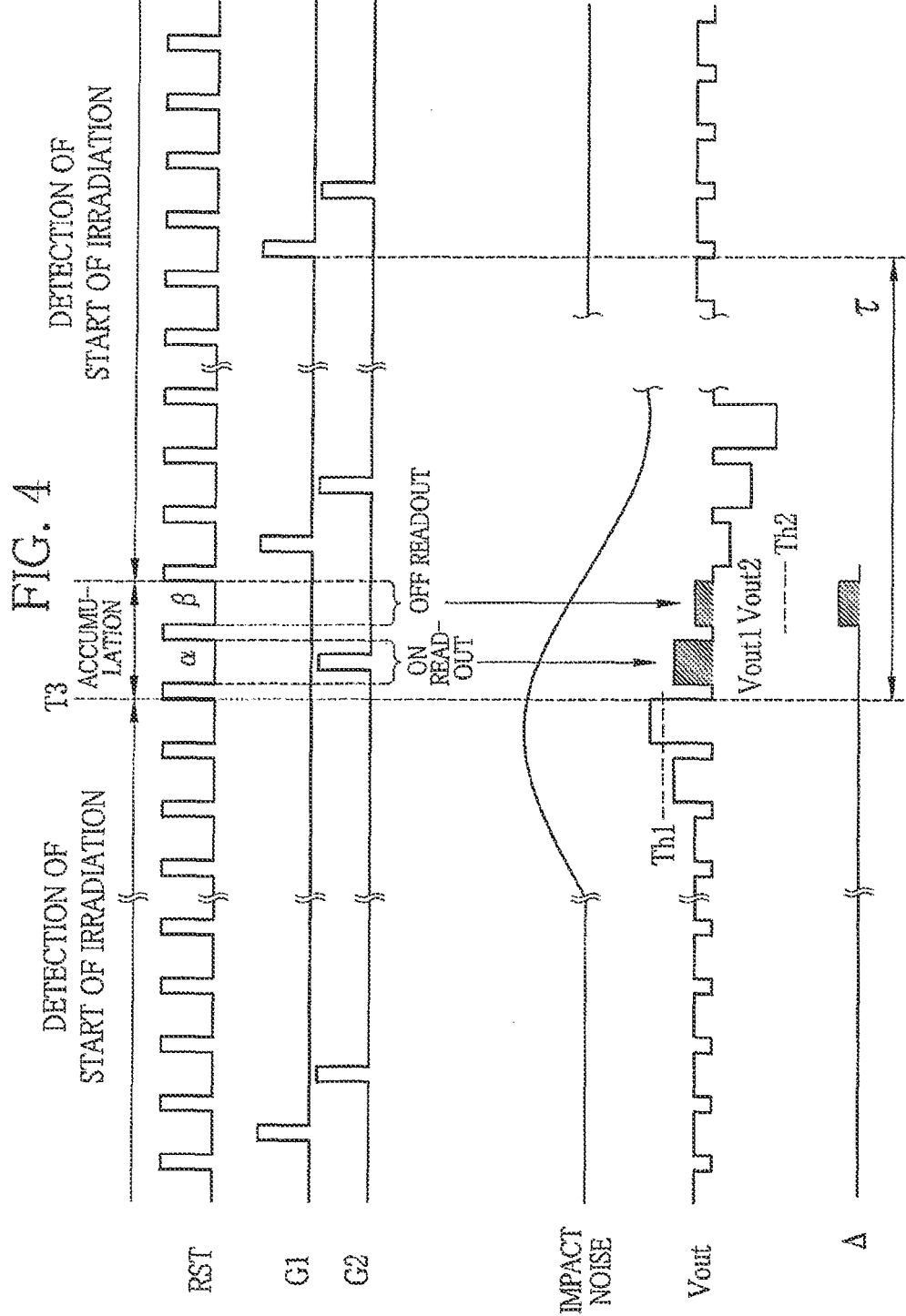
FIG. 4 is a timing chart showing a signal waveform formed by impact noise.

As shown in FIG. 4, when the impact noise occurs, the voltage signal Vout shows a waveform on which the impact noise is superposed on the dark charge noise. The dark charge noise is caused by electric charge and occurs in the pixels 37 whenever the FPD 25 is driven, irrespective of the presence or absence of the incident X-rays. In the integrating amplifier 66, the dark charge noise is reset by inputting the reset pulse RST thereto. On the other hand, the impact noise is directly superposed on the output of the integrating amplifier 66 regardless of the signal charge accumulated in the integrating amplifier 66. Accordingly, the reset pulse RST cannot reset the impact noise.

As described above, the threshold value Th1 is set greater than the dark charge noise. The voltage signal Vout is less than the threshold value Th1 when composed only of the dark charge noise. However, when the impact noise is superposed on the dark charge noise, the voltage signal Vout may reach a value greater than or equal to the threshold value Th1 even without the X-ray emission. Here, at a time T3, the voltage signal Vout exceeds the threshold value Th1 due to the impact noise.

During the irradiation detecting operation, when the voltage signal Vout reaches greater than or equal to the threshold value Th1, the controller 54 turns off the TFT 43 of every pixel 37, in the same manner as an example shown in FIG. 3, to start the accumulation operation. Then, the controller 54 commands the gate driver 52 to input the gate pulse (G2) to the scan line 47 to which the detection pixel 61 is connected, in synchronization with the first reset pulse RST inputted to the integrating amplifier 66 after the accumulation operation is started. Thereby, the TFT 43 of the detection pixel 61 is turned on throughout a period α. The first voltage signal Vout1 (ON readout) is inputted to the controller 54. From the subsequent period β and on, the controller 54 turns off the TFT 43 of the detection pixel 61 to start accumulating the signal charge in the detection pixel 61. The second voltage signal Vout2 (OFF readout), obtained in the period β, is inputted to the controller 54.

Then, the controller 54 calculates the difference Δ between the first and second voltage signals Vout1 and Vout2, and compares the difference Δ with the threshold value Th2 to judge whether the change in the voltage signal Vout is caused by the X-ray irradiation. In this example, the change in the voltage signal Vout is caused by the impact noise, so the first voltage signal Vout1 is a value in which the impact noise is superposed on the dark charge noise occurred during the period α. On the other hand, the second voltage signal Vout2 (OFF readout) includes the impact noise but not the dark charge noise occurred in the period β.

It is considered that the impact noise is substantially constant throughout the periods α and β. By calculating the difference Δ, the impact noise in the period α is cancelled out by the impact noise in the period β. Namely, the difference Δ is of the order of the dark charge noise occurred in the detection pixel 61 during the period α, and is extremely small compared with the difference Δ caused by the X-ray irradiation. The controller 54 compares the difference Δ with the threshold value Th2, and judges that the change in the voltage signal Vout is caused by the impact noise.

Upon judging that the change in the voltage signal Vout is caused by the impact noise, the controller 54 turns on the TFT 43 of every pixel 37 to abort the accumulation operation and resume the irradiation detecting operation. The controller 54 starts monitoring the voltage signal Vout1 after a time τ, necessary for the impact noise to attenuate, elapses from the time T3. This prevents the accumulation operation from being caused by the same impact noise. The time τ is considered to be approximately constant regardless of the magnitude or the like of the impact, and previously set.

As described above, in the X-ray imaging system 10, the electronic cassette 14 monitors the output of the detection pixel 61 to start the accumulation operation based on the change in the voltage signal Vout. Thereby, the electronic cassette 14 performs radiography in synchronization with the X-ray irradiation from the X-ray source 12 even if the electronic cassette 14 is not connected to the X-ray source 12 including devices connected to the X-ray source 12. In the X-ray imaging system 10, the electronic cassette 14 starts the accumulation operation when the voltage signal Vout changes, and then successively obtains the first and second voltage signals Vout1 and Vout2 after the start of the accumulation operation. Based on the difference Δ between the first and second voltage signals Vout1 and Vout2, the controller 54 judges whether the change in the voltage signal Vout is caused by the X-ray irradiation or the impact noise. When the change in the voltage signal Vout is caused by the X-ray irradiation, the radiography is continued. On the other hand, when the change in the voltage signal Vout is caused by the impact noise, the radiography is stopped and the irradiation detecting operation is resumed immediately. Thereby, meaningless radiography caused by the impact noise is prevented.

In the first embodiment, the voltage signal Vout1 (ON readout) and the voltage signal Vout2 (OFF readout) are obtained successively, and it is judged whether the X-irradiation or the impact noise takes place based on the difference Δ between the voltage signals Vout1 and Vout2, by way of example. Alternatively, two voltage signals (both ON readouts) may be obtained successively. The judgment may be made based on the difference Δ between these two voltage signals.

(Second Embodiment)

In this embodiment, the start of the X-ray irradiation is judged based on two successive voltage signals (both ON readouts). The configuration of the X-ray imaging system 10 of this embodiment is similar to that in the first embodiment, so the description thereof is omitted.

Figure 5:
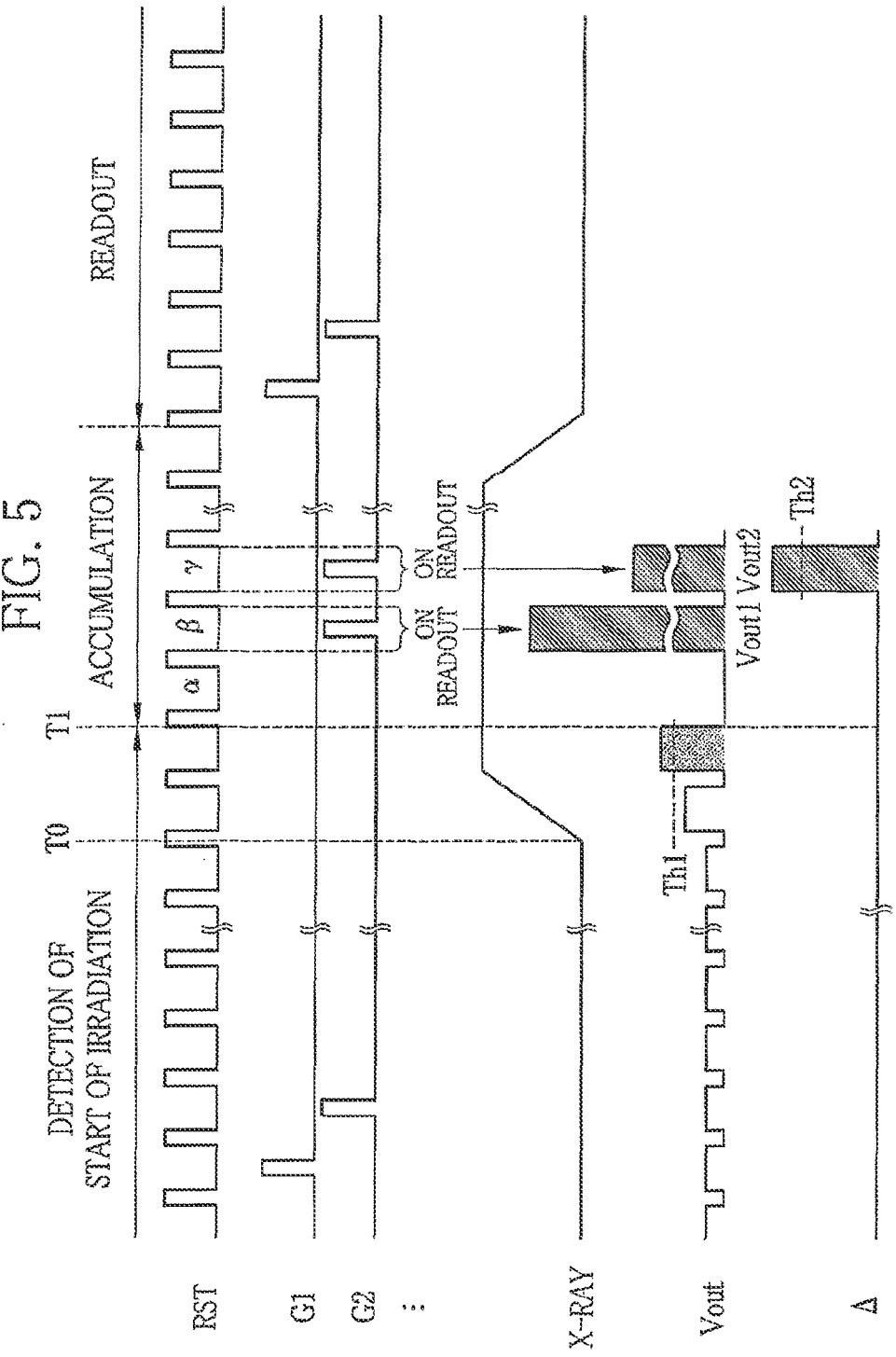
FIG. 5 is a timing chart showing a signal waveform by the X-ray irradiation in a second embodiment.

As shown in FIG. 5, before the time T0 at which the X-ray source 12 starts emitting the X-rays, the voltage signal Vout, the gate pulses G1 to Gn, and the like behave similarly to those in the first embodiment. After the X-ray source 12 starts emitting the X-rays at the time T0, the controller 54 regards that the X-ray irradiation is started at a time T1 at which the voltage signal Vout reaches a value greater than or equal to the threshold value Th1. The controller 54 turns off the TFT 43 of every pixel 37 at the time T1 to start the accumulation operation.

Next, the controller 54 inputs the gate pulse (G2) to the scan line 47 to which the detection pixel 61 is connected, in synchronization with the second reset pulse RST. Thereby, after the start of the accumulation operation, in the period β between the reset pulses RST, the TFT 43 of the detection pixel 61 is turned on. The signal charge generated in the detection pixel 61 during the period α is read out to the integrating amplifier 66 in the period β. The voltage signal Vout (ON readout) in the period β is inputted as the first voltage signal Vout1 to the controller 54.

After the ON readout in the period β, in a next period γ between the reset pulses RST, the controller 54 commands the gate driver 52 to input the gate pulse (G2) again to the scan line 47 to which the detection pixel 61 is connected. Thereby, the TFT 43 of the detection pixel 61 is turned on in the period γ. The signal charge generated in the detection pixel 61 during the period γ is read out to the integrating amplifier 66. Thereby, in the period γ, the second voltage signal Vout2 (ON readout) is inputted to the controller 54.

The controller 54 calculates the difference Δ between the first and second voltage signals Vout1 and Vout2 obtained successively by the ON readouts. The difference Δ is compared with the threshold value Th2 to judge whether the change in the voltage signal Vout is caused by the X-ray irradiation.

The first voltage signal Vout1 is generated from the signal charge accumulated in the detection pixel 61 from the beginning of the accumulation operation to the end of the period β (approximately throughout the periods α and β). On the other hand, the second voltage signal Vout2 is generated from the signal charge accumulated in the detection pixel 61 during the period γ.

The reset pulse RST is inputted to the integrating amplifier 66 at regular time intervals. An amount of X-ray dose is constant. Accordingly, the values of the signal charge generated in the detection pixel 61 in the respective periods α, β and γ are approximately equivalent. In this embodiment, the difference Δ corresponds to a value of the signal charge generated in the detection pixel 61 from the time T1 at the beginning of the accumulation operation to the input of the reset pulse RST which begins the period β. Accordingly, the difference Δ is greater than the threshold value Th2, so the controller 54 judges that the X-ray irradiation takes place.

When the controller 54 judges that the X-ray irradiation is started, the controller 54 allows continuing the accumulation operation, started from the time T1, until the predetermined time elapses. Thereafter, the controller 54 switches the accumulation operation to the readout operation. Thus, the radiography is carried out.

Figure 6:
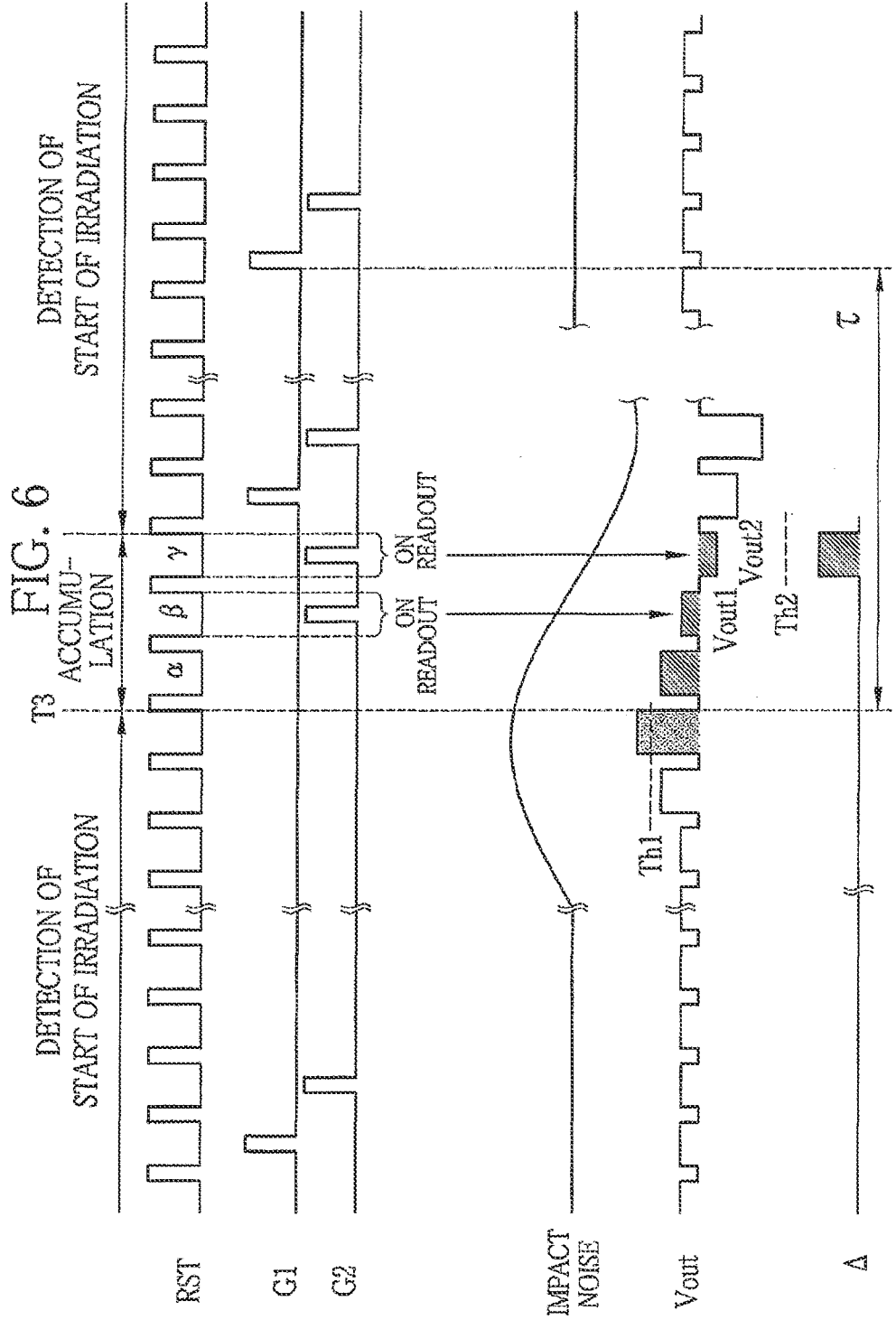
FIG. 6 is a timing chart showing a signal waveform formed by impact noise in the second embodiment.

On the other hand, as shown in FIG. 6, when impact noise occurs, the controller 54 turns off the TFT 43 of every pixel 37 to start the accumulation operation at a time T3 at which the value of the voltage signal Vout reaches greater than or equal to the threshold value Th1. Then, in the period β, the controller 54 allows reading the signal charge from the detection pixel 61. Thereby, the first voltage signal Vout1 (ON readout) is inputted to the controller 54. In the period γ, the controller 54 inputs the gate pulse (G2) to the scan line 47, to which the detection pixel 61 is connected, to allow reading the signal charge from the detection pixel 61. Thereby, the second voltage signal Vout2 (ON readout) obtained during the period γ is inputted to the controller 54.

The controller 54 calculates the difference Δ between the first and second voltage signals Vout1 and Vout2. In this embodiment, in the first voltage signal Vout1, the impact noise in the period β is superposed on the dark charge noise caused by the dark charge accumulated from the beginning of the accumulation operation to the end of the period β. In the second voltage signal Vout2, the impact noise in the period γ is superposed on the dark charge noise caused by the dark charge occurred in the period γ. Accordingly, the difference Δ calculated by the controller 54 takes a value as follows. For example, when the sign of the value of the impact noise in the first voltage signal Vout1 is the same as that in the voltage signal Vout2, the impact noise superposed in the period β and the impact noise superposed in the period γ cancel out each other and is reduced in the difference Δ. The value of the dark charge noise occurred during the period β and that occurred during the period γ are approximately equivalent, so they cancel out each other to give approximately "0". Thus, the difference Δ is of the order of the value corresponding to the dark charge noise accumulated during the period α, and remains less than the threshold value Th2. On the other hand, in an example shown in FIG. 6, when the signs of the values of the impact noise are opposite in the periods β and γ, the value of the dark charge noise in the period β and that in the period γ cancel out each other to give approximately "0" similar to the above, but the values of the impact noise in the periods β and γ are added. However, the values corresponding to the impact noise are extremely small when the signs of the values are opposite. Therefore, the difference Δ remains less than the threshold value Th2.

The controller 54 judges that the change in the voltage signal Vout is caused by the impact noise based on the fact that the difference Δ is less than the threshold value Th2. Upon this judgment, the controller 54 turns on the TFT 43 of every pixel 37 to abort the accumulation operation and resume the irradiation detecting operation. Then, the controller 54 starts monitoring the voltage signal Vout1 after the time τ, necessary for the impact noise to attenuate, elapses from the time T3.

Figure 7:
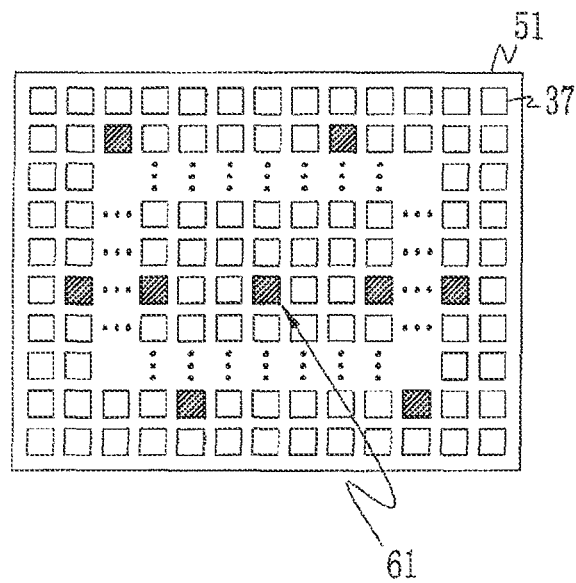
FIG. 7 is an explanatory view showing detection pixels by way of example.

In the first and second embodiments, there is only single detection pixel 61 by way of example. As shown in FIG. 7, there may be two or more detection pixels 61. For example, all the pixels 37 of the single row may be used as the detection pixels 61. When there are two or more detection pixels 61, the judgment is made for each detection pixel 61 based on an output value of the integrating amplifier 66 of the signal line 48 to which the detection pixel 61 is connected, for example. When the number of the detection pixels 61, with the change in the voltage signal Vout judged to be caused by the X-ray irradiation, is greater than or equal to a predetermined number, it is judged that the X-ray irradiation takes place. When the number of the above detection pixels 61 is less than the predetermined number, it is judged that the impact noise takes place. The change in the voltage signal Vout is detected in the similar manner.

By setting two or more detection pixels 61, failure in detecting the X-ray irradiation is prevented, for example, when one of the detection pixels 61 is located at a position corresponding to a region which does not allow the X-rays to pass therethrough. Additionally, the detection and the judgment are carried out more accurately.

Figure 8:
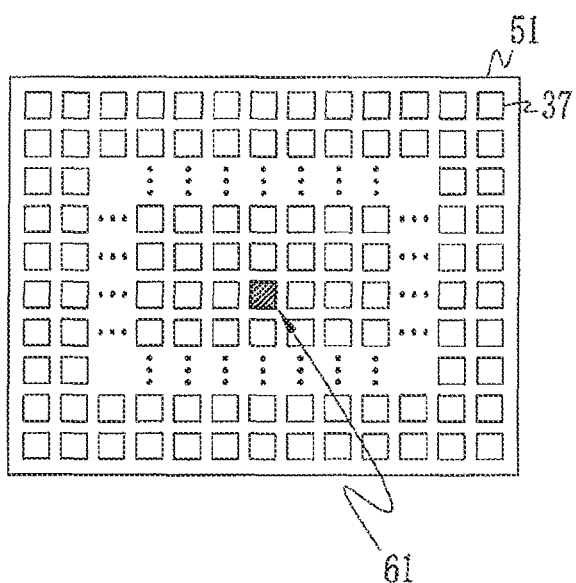
FIG. 8 is an explanatory view showing the detection pixel located close to the center of an imaging area by way of example.

In the first and second embodiments, for the sake of convenience in illustration, the single detection pixel 61 is located at a corner portion of the imaging area 51 by way of example. As shown in FIG. 8, the detection pixel 61 may be located at the center or close to the center of the imaging area 51. When two or more detection pixels 61 are provided, it is preferable that at least one of the detection pixels 61 is located at the center or close to the center of the imaging area 51.

Thereby, the start of the X-ray irradiation is judged accurately even if the radiography is performed with the center of the X-ray irradiation or of the imaging field shifted from the center of the imaging area 51.

In the first and second embodiments, by way of example, the threshold value Th1 is used for the detection of the change in the voltage signal Vout, and the threshold value Th2 is used for judging the cause of the change in the voltage signal Vout. The threshold values Th1 and Th2 may take the same value.

In the first and second embodiments, the threshold value Th2 is set greater than or equal to the threshold value Th1 by way of example. Alternatively, the threshold value Th2 may be set less than the threshold value Th1. It is preferable that the threshold value Th1 is as small as possible. The smaller the threshold value Th1, the shorter the time required for detecting the start of the X-ray irradiation. This reduces an amount of X-rays wasted before this detection. On the other hand, it is preferable that the threshold value Th2 is as large as possible. This is because the threshold value Th2 is used for judging the cause of the change in the voltage signal Vout. When the X-ray irradiation takes place, the difference Δ takes a large value relative to the amplitude of the impact noise. By setting the large threshold value Th2 (for example, larger than the threshold value Th1), whether the change in the voltage signal Vout is caused by the X-ray irradiation is judged more accurately.

In the first and second embodiments, when the irradiation detecting operation is switched to the accumulation operation, the judgment whether the X-ray irradiation takes place is made in the period α, that is, the first period between the reset pulses RST and the subsequent period β, by way of example. The judgment maybe carried out at least before the time τ, necessary for the impact noise to attenuate, elapses. It is possible to judge after the time τ elapses. However, this holds up the restart of the irradiation detecting operation. Similarly, it is preferable to judge whether the X-ray irradiation takes place as soon as possible, after the irradiation detecting operation is switched to the accumulation operation as described in the first and second embodiments.

In the first and second embodiments, the signal charge of the pixels 37 (including the detection pixel 61) of the single row is read out to detect the X-ray irradiation. Accordingly, the pixel value of the pixels 37 of the row which includes the detection pixel 61 may be small in the X-ray image data obtained with the electronic cassette 14, making the X-ray image defective. In this case, the pixel value of the pixels 37 of the row which includes the detection pixel 61 is corrected through interpolation or the like by the correction section 31 of the console 21 before being outputted to the monitor 22. The pixel value may be corrected through gain adjustment by the integrating amplifier 66 when the pixels 37 of the row which includes the detection pixel 61 is read out.

In the first and second embodiments, the correction section 31 is provided in the console 21 by way of example. Alternatively, the correction section 31 may be provided to the electronic cassette 14.

In the first and the second embodiments, during the standby state, the pixels 37 are reset on a row-by-row basis sequentially by way of example (sequential resetting). Alternatively, all the pixels 37 maybe reset at a time in the standby state (simultaneous resetting). In the above embodiments, the sequential resetting of the pixels 37 is repeated during the standby state by way of example. The pixels 37 may be reset at any timing and frequency unless this reset does not hinder the irradiation detecting operation. For example, a case where the voltage signal Vout jumps greater than or equal to the threshold value Th1, with no X-ray emission and no impact noise, as soon as the TFT 43 of the detection pixel 61 is turned on in the irradiation detecting operation should be avoided. The pixels 37 may be reset at least immediately before being switched to the irradiation detecting operation.

In the first and second embodiments, the accumulation operation is started when the voltage signal Vout1 is greater than the threshold value Th1, and then the judgment is made to continue or abort the accumulation operation. Alternatively, The accumulation operation may be started when it is judged that the change in the voltage signal Vout is caused by the X-ray irradiation. In third and fourth embodiments described below, the accumulation operation is started based on this judgment. In each of the third and fourth embodiments, the configuration of the X-ray imaging system is similar to the X-ray imaging system 10 of the first and second embodiments, so description thereof is omitted. Description on operations similar to those in the first and second embodiments is also omitted.

(Third Embodiment)

As shown in FIG. 9, when the irradiation detecting operation is started, the controller 54 successively obtains the voltage signal Vout1 (ON readout) and the voltage signal Vout2 (OFF readout) from the detection pixel 61. The voltage signals Vout1 and Vout2 are obtained in synchronization with the reset pulses RST, respectively. Namely, the controller 54 obtains the voltage signal Vout1 in response to the input of the gate pulse G2, and then obtains the voltage signal Vout2. Then, the controller 54 calculates the difference Δ between the voltage signals Vout1 and Vout2, and compares the difference Δ with a threshold value Th3.

Before the X-ray irradiation, each of the voltage signals Vout1 and Vout2 is at a noise level, so the difference Δ is approximately "0". Namely, the difference Δ remains less than the threshold value Th3 before the X-ray irradiation. In this state, the controller 54 does not judge the start of the X-ray irradiation. When the X-rays are applied at a time T0, the voltage signal Vout takes a value corresponding to the amount of the X-rays incident on the detection pixel 61. When the voltage signals Vout1 and Vout2 are successively obtained from the detection pixel 61 during the X-ray irradiation, the difference Δ is greater than or equal to the threshold value Th3. The controller 54 judges that the X-ray irradiation is started when the difference Δ is greater than or equal to the threshold value Th3. Upon this judgment, the controller 54 allows starting the accumulation operation.

As shown in FIG. 10, when the impact noise occurs, the controller 54 successively obtains the voltage signals Vout1 and Vout2 and calculates their difference Δ, similar to the above. The impact noise remains approximately constant in an ultrashort time in which the voltage signals Vout1 and Vout2 are obtained successively. Accordingly, the difference Δ is approximately "0", even if each of the voltage signals Vout1 and Vout2 exceeds the noise level due to the impact noise, and remains less than threshold value Th3. In this state, the controller 54 does not judge that the X-ray irradiation is started even if the impact noise occurs, and continues the irradiation detecting operation.

As described above, whether the X-ray irradiation is started is judged based on the difference Δ. Thereby, the start of the X-ray irradiation is judged accurately. In this embodiment, the start of the X-ray irradiation is judged more accurately and quickly, compared with the X-ray imaging system 10 of the first and second embodiments.

In this embodiment, the magnitude of difference Δ between the voltage signal Vout1 (ON readout) and the voltage signal Vout2 (OFF readout) is used for judging the start of the X-ray irradiation by way of example. Alternatively, the magnitude of a difference Δ between the voltage signals Vout1 and Vout2 (both ON readouts) obtained successively may be used for the judgment, which will be described as a fourth embodiment.

(Fourth Embodiment)

As shown in FIG. 11, when the irradiation detecting operation is started, the controller 54 successively obtains the first and second voltage signals Vout1 and Vout2 (both ON readouts). The voltage signals Vout1 and Vout2 are obtained in synchronization with the reset pulses RST, respectively. In this embodiment, two gate pulses (G2) are input successively to the row to which the detection pixel 61 is connected. The voltage signals Vout1 and Vout2 are obtained in synchronization with the two successive gate pulses G2, respectively. The controller 54 calculates the difference Δ between the voltage signals Vout1 and Vout2, and compares the difference Δ with the threshold value Th3.

Before the X-ray irradiation, each of the voltage signals Vout1 and Vout2 is at a noise level. Accordingly, the difference Δ is approximately "0". In other words, the difference Δ remains less than the threshold value Th3 before the X-ray irradiation. In this state, the controller 54 does not judge the start of the X-ray irradiation. When the X-rays are applied at a time T0, the voltage signal Vout takes a value corresponding to the amount of the X-rays incident on the detection pixel 61. When the voltage signals Vout1 and Vout2 (both ON readouts) are obtained successively during the X-ray irradiation, the signal value of the voltage signal Vout1 is greater than that of the voltage signal Vout2. This is because the voltage signal Vout1 corresponds to the signal charge accumulated in the detection pixel 61 from the start of the X-ray irradiation until the voltage signal Vout1 is obtained. On the other hand, the voltage signal Vout2 corresponds to the signal charge accumulated in the detection pixel 61 only during a period between the two reset pulses RST, after the voltage signal Vout1 is obtained. In this case, the difference Δ between the voltage signals Vout1 and Vout2 exceeds the noise level and reaches greater than or equal to the threshold value Th3. The controller 54 judges that the X-ray irradiation is started when the difference Δ is greater than or equal to the threshold value Th3. Thereby, the controller 54 allows starting the accumulation operation.

As shown in FIG. 12, when the impact noise occurs, the controller 54 successively obtains the voltage signals Vout1 and Vout2, similar to the above. The controller 54 calculates the difference Δ. The impact noise remains approximately constant in an ultrashort time in which the voltage signals Vout1 and Vout2 are obtained successively. The difference Δ is approximately "0", even if each of the voltage signals Vout1 and Vout2 exceeds the noise level due to the impact noise, and remains less than threshold value Th3. In this state, the controller 54 continues the irradiation detecting operation even if the impact noise occurs.

As described above, whether the X-ray irradiation is started is judged based on the difference Δ between the voltage signals Vout1 and Vout2 (both ON readouts). The controller 54 accurately judges whether the X-ray irradiation takes place without the influence of the impact noise, similar to the third embodiment. In this embodiment, the start of the X-ray irradiation is judged more accurately and quickly, compared with the first and second embodiments.

In the third and fourth embodiments, the voltage signals Vout1 and Vout2 are obtained from the detection pixel 61 by way of example. In this case, the voltage signals Vout1 and Vout2 are obtained in synchronization with the pixel reset operation of the pixels 37 (including the detection pixel 61) of the same row. Because of this, the judgment may be slightly delayed when the pixels 37 of another row are reset, depending on the irradiation timing of the X-rays. It is preferable to prevent the delay in the judgment as follows.

The detection pixel 61 is selected from the pixels 37 to judge the start of the X-ray irradiation, so the configuration of the detection pixel 61 is the same as those of the remaining pixels 37. Here, the pixels 37 of the same column (or all the pixels 37) are used as the detection pixels 61. As shown in FIG. 13, when the start of the X-ray irradiation is judged based on the difference Δ between the voltage signal Vout1 (ON readout) and the voltage signal Vout2 (OFF readout), an input interval between the gate pulses for the pixel reset operation is adjusted such that the ON readout and the OFF readout of the pixels 37 are carried out successively for each row. As shown in FIG. 14, when the start of the X-ray irradiation is judged based on the difference Δ between the voltage signals Vout1 and Vout2 (both ON readouts), two gate pulses are inputted successively to each row to carry out the respective ON readouts to perform the pixel reset operation. Thereby, the start of the X-ray irradiation is judged incessantly without the delay irrespective of the irradiation timing.

In the first to fourth embodiments, during the irradiation detecting operation, the pixel reset operation of the sequential reset method is performed by way of example. Alternatively, the TFT 43 of every pixel 37 may be turned on during the irradiation detecting operation. This keeps every pixel 37 in the reset state and thus prevents offset noise even if the accumulation operation begins simultaneously with the judgment of the start of the X-ray irradiation. When the TFTs 43 of all the pixels 37 are not turned on during the irradiation detecting operation, the dark charge may accumulate in the pixels 37 and affect the image quality if the duration of the irradiation detecting operation is long. Accordingly, it is preferable to reset the pixels 37 when the irradiation detecting operation is switched to the accumulation operation after the start of the X-ray irradiation is judged.

In the first to fourth embodiments, the difference Δ between the first and second voltage signals Vout1 and Vout2 is calculated, taking the plus and minus signs into account. Alternatively, the difference Δ between the absolute values of the voltage signals Vout1 and Vout2 may be calculated.

In the first to fourth embodiments, the FPD 25, being the panel of the indirect conversion type is described by way of example. Alternatively, a panel of the direct conversion type may be used.

Various changes and modifications are possible in the present invention and may be understood to be within the present invention.

What is claimed is:

1. A radiation image detecting device for imaging a subject irradiated with radiation from a radiation source to obtain a radiological image, the radiation image detecting device comprising:

a plurality of pixels arranged in two-dimensions along row and column directions in an imaging area, each pixel of the plurality of pixels generating signal charge corresponding to an amount of the radiation incident on the pixel, each pixel of the plurality of pixels having a switching element for controlling reading of the signal charge;

a plurality of scan lines extending in the row direction, each scan line of the plurality of scan lines being connected to gate electrodes of the respective switching elements of the corresponding pixels;

a plurality of signal lines extending in the column direction, each signal line of the plurality of signal lines being connected to the corresponding pixels through the switching elements;

a drive section for turning off the switching element of the pixel to allow performing accumulation operation and for turning on the switching element of the pixel to allow performing readout operation, the signal charge generated in the pixels being accumulated in the accumulation operation, the signal charge accumulated being read out through the signal line connected to the pixel in the readout operation; and a controller using at least one of the plurality of pixels as a detection pixel for judging start of irradiation with the radiation, the controller successively obtaining two output values, being first and second signal values, from the signal line connected to the detection pixel, the controller judging whether the irradiation with the radiation is started based on a difference between the first and second signal values, the controller controlling the drive section based on the judgment.

2. The radiation image detecting device according to claim 1, wherein the controller obtains a first difference between the first and second signal values, and judges that the irradiation is started when the first difference is greater than or equal to a first threshold value.

3. The radiation image detecting device according to claim 2, wherein the controller carries out the steps of:
starting the accumulation operation through the drive section when the first difference reaches greater than or equal to a second threshold value during irradiation detecting operation;
continuing the accumulation operation for a predetermined time to obtain the radiological image when it is judged, after a start of the accumulation operation, that the irradiation is started; and
aborting the accumulation operation and resuming the irradiation detecting operation when the controller judges that the irradiation is not started.

4. The radiation image detecting device according to claim 3, further including a correction section for correcting a pixel value of the pixels of a row in which the detection pixel is located.

5. The radiation image detecting device according to claim 2, wherein the controller carries out the step of starting the accumulation operation through the drive section to obtain the radiological image when the controller judges that the irradiation is started during the irradiation detecting operation.

6. The radiation image detecting device according to claim 1, wherein the first signal value is obtained when the switching element of the detection pixel is in an ON state, and the second signal value is obtained when the switching element of the detection pixel is in an OFF state.

7. The radiation image detecting device according to claim 1, wherein the first and second signal values are obtained when the switching element is in an ON state.

8. The radiation image detecting device according to claim 1, wherein the controller using two or more of the plurality of pixels as detection pixels.

9. The radiation image detecting device according to claim 1, wherein the detection pixel is located close to a center of the imaging area.

10. The radiation image detecting device according to claim 1, wherein the signal line is connected to an integrating amplifier for converting the signal charge into a voltage signal.

11. A method for detecting start of irradiation with radiation from a radiation source to a radiation image detecting device, the radiation image detecting device having a plurality of pixels arranged in two dimensions and a plurality of switching elements used for accumulation and readout of signal charge in the respective pixels, the method comprising using one or more processors to perform the steps of:
using at least one of the plurality of pixels as a detection pixel;
successively obtaining output values, being a first and second signal values, of a signal line connected to the detection pixel;
judging whether the irradiation with the radiation is started based on a difference between the first and second signal values; and
controlling accumulation operation of each of the pixels in accordance with a result of the judgment.

12. The method according to claim 11, wherein judging whether the irradiation with the radiation is started when the difference between the first and second signal values is greater than or equal to a first threshold value.

13. The method according to claim 12, wherein successively obtaining output values comprises obtaining the first signal value when the switching element is in an ON state, and the second signal value when the switching element is in an OFF state.

14. The method according to claim 12, wherein successively obtaining output values comprises obtaining the first and second signal values when the switching element is in an ON state.

15. The method according to claim 12, further including the steps of:
starting the accumulation operation through a drive section when the difference is greater than or equal to a second threshold value during irradiation detecting operation;
continuing the accumulation operation for a predetermined time to obtain the radiological image when it is judged, after a start of the accumulation operation, that the irradiation is started; and
aborting the accumulation operation and resuming the irradiation detecting operation when it is judged that the irradiation is not started.

16. The method according to claim 12, further including the step of starting the accumulation operation through a drive section to obtain the radiological image when it is judged that the irradiation is started during the irradiation detecting operation.

* * * * *